United States Patent [19]
Carnahan et al.

[11] Patent Number: 5,830,857
[45] Date of Patent: Nov. 3, 1998

[54] METHOD OF TREATING EPILEPSY

[75] Inventors: Josette Françoise Carnahan, Newbury Park, Calif.; Antoine Depaulis; Paul Feltz, both of Strasbourg, France; Yves Larmet, Schiltigheim, France; Christian Marescaux, Strasbourg, France; Hiroyuki Nawa, Niigata, France

[73] Assignee: Amgen Inc., Thousand Oaks, Calif.

[21] Appl. No.: 502,348

[22] Filed: Jul. 14, 1995

[51] Int. Cl.⁶ ............ A61K 38/00; C12P 21/06; C12N 15/00; C07K 3/00
[52] U.S. Cl. .......... 514/12; 530/350; 530/387.9; 530/399; 435/69.1
[58] Field of Search .............. 530/399, 350, 530/387.9; 435/69.1; 514/12

[56] References Cited

U.S. PATENT DOCUMENTS 5,180,820  1/1993  Barde et al. .................. 530/399
5,229,500  7/1993  Barde et al. .................. 530/399

OTHER PUBLICATIONS

Thoenen, et al., *TINS*, vol. 14, No. 5, pp. 165–170 (1991).
Lindvall et al., *TINS.*, vol. 17, No. 11, pp. 490–496 (1994).
Mody, *Brain Pathology*, vol. 3, pp. 395–403 (1993).
Gall, Experimental Neurology, vol. 124, pp. 150–166 (1993).
Goddard et al., *Experimental Neurology*, vol. 25, pp. 295–330 (1969).
Hirsch et al., *Epilepsy Res.*, vol. 11, pp. 159–166 (1992).
Shen et al., *PNAS USA*, vol. 91, pp. 8920–8924 (1994).

*Primary Examiner*—Cecilia J. Tsang
*Assistant Examiner*—P. L. Touzeau
*Attorney, Agent, or Firm*—Richard J. Mazza; Ron Levy; Steven M. Odre

[57] ABSTRACT

A method is described for the therapeutic use of brain-derived neurotrophic factor (BDNF) to treat epilepsy.

10 Claims, 3 Drawing Sheets

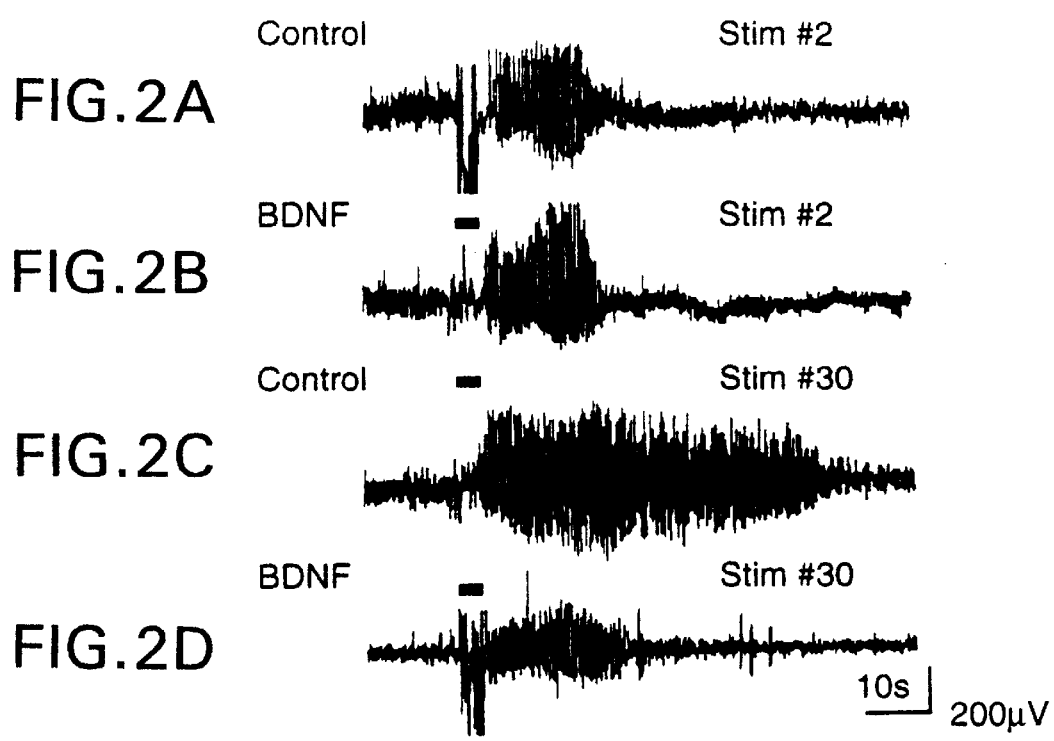

METHOD OF TREATING EPILEPSY

FIELD OF THE INVENTION

This invention relates to a method for the therapeutic treatment of epilepsy in mammals comprising administering an effective amount of brain-derived neurotrophic factor (BDNF).

BACKGROUND OF THE INVENTION

Epilepsies comprise a remarkably diverse collection of disorders that affect 1–4% of the population in the United States alone. Current therapy is symptomatic. Available drugs reduce seizure frequency in the majority of patients, but it is estimated that only about forty percent are free of seizures despite optimal treatment. From a clinical point of view three types of epilepsy have been defined: (1) petit mal, which is characterized by the absence of seizures or small seizures, (2) grand mal, which comprise generalized catatonic seizures, and (3) complex partial, which is often localized in temporal lobe seizures. The third form is the most common, and it is often resistant to medical treatment. Surgical resection is often the only form of treatment that eliminates seizure in the majority of these patients.

The nerve growth factor family of polypeptides referred to as neurotrophins, for example, NGF, BDNF, NT-3, etc., is known to be involved in the development of the central nervous system, as well as in adult brain plasticity; Thoenen, Trends in Neuroscience, Volume 14, page 165 et seq. (1991); Lindvall et al., Trends in Neuroscience, Volume 17, page 490 et seq. (1994). Epileptogenesis is a widely studied example of such long term neuroplasticity in adults, and recently developed data suggests the involvement of neurotrophins in the cascade of physiological events occurring during seizure development Mody, Brain Pathology, Volume 3, page 395 et seq. (1993); Gall Experimental Neurology, volume 124, page 150 et seq. (1993). BDNF appears to be a critical neurotrophin which is involved in these processes because the expression of this protein and its encoding messenger RNA increases in the hippocampus, amygdala and cortex of test rats following convulsive seizures. Nevertheless, the physiological significance of this neurotrophin in the context of epileptogenesis remains to be determined.

SUMMARY OF THE INVENTION

It has now been discovered that the administration of BDNF blocks the development of epileptic seizures, as determined in an animal model of epileptogenesis. These results provide the first in vivo evidence for a protective role of BDNF in the regulation of neuroplasticity in the adult brain and constitute a basis for this invention, which comprises a method for treating epilepsy in mammals by the administration of a therapeutically effective amount of BDNF.

By "therapeutically effective amount" it is meant an amount that is sufficient to prevent, retard or ameliorate epileptic seizures in vivo.

BRIEF DESCRIPTION OF THE FIGURES

FIG. 2 depicts electroencephalographic recordings of cortical afterdischarges following hippocampal stimulation in the rat model of FIG. 1. The first two graphs show the afterdischarges following the second hippocampal stimulation in a phosphate buffered solution(PBS)-perfused rat (first graph) and a BDNF-perfused rat (second graph). The last two graphs show the afterdischarges following the thirtieth hippocampal stimulation in a PBS-perfused rat (third graph) and a BDNF-perfused rat (fourth graph).

DETAILED DESCRIPTION OF THE INVENTION

BDNF can be administered in accordance with this invention by any effective route which delivers effective amounts of BDNF to the affected site in the brain. Typically, administration to the central nervous system, and especially, localized delivery by intraventricular or intraparenchymal administration to the brain, are preferred as the quickest and most direct means. Local infusion by injection, by means of a catheter or a reservoir implant are preferred. However, any other means which effectively delivers therapeutic amounts of biologically active BDNF to the affected site in the brain can be alternatively employed, for example, intravenous, intramuscular, subcutaneous, etc., as properly formulated.

Also contemplated as being within the scope of the term "administration" is the administration of BDNF in the form of transplanted tissue pretreated with BDNF or containing the transfected DNA for BDNF operably linked to an expression vector for in situ expression.

Typically, BDNF will be administered by this invention in the form of a pharmaceutically acceptable buffered solution or buffered saline solution. It is anticipated that for human administration an effective dose will be from about 0.02 to about 0.25 milligrams per kilogram of body weight per day, although the skilled practitioner will understand that particular amounts may vary depending on factors such as the condition and age of the patient, severity of the illness, side effects, if any, etc.

To facilitate delivery it may be desirable in certain instances to employ BDNF in the form of a pharmaceutical composition comprising liposomes, microparticles, or microcapsules to achieve sustained release of bioactive material. Implantation of cells transfected with the BDNF gene construct, as mentioned, might be an alternative as well.

Any form of biologically active BDNF will be acceptable for the practice of this invention, for example, purified native, chemically synthesized, or recombinantly derived. Preferably, recombinant BDNF is employed, principally for reasons of ease of production. Recombinant BDNF can be produced using any of the methods of heterologous expression known in the art, for example, by the methods referred to in U.S. Pat. Nos. 5,180,820 and 5,229,500, the disclosures of which are hereby incorporated by reference. Particularly preferred for use in the described therapeutic method is recombinant human BDNF made in *E. coli* and having the sequence:

MHSDPARRGELSVCDSISEWVTAADKKTAVDMSGGTVTVLEKVPVSKGQLKQYFYE

TKCNPMGYTKEGCRGIDKRHWNSQCRTTQSYVRALTMDSKKRIGWRFIRIDTSCVC

TLTIKRGR (SEQ ID NO: 1).

Also possible for use in the practice of this invention are derivatives of BDNF that have been designed to enhance biological properties and/or delivery characteristics, such as BDNF chemically linked to polymers, for example, polyethylene glycol-modified BDNF.

The invention is further described with reference to the following example and test results.

Animal Model of Epileptogenesis

Figure 1:
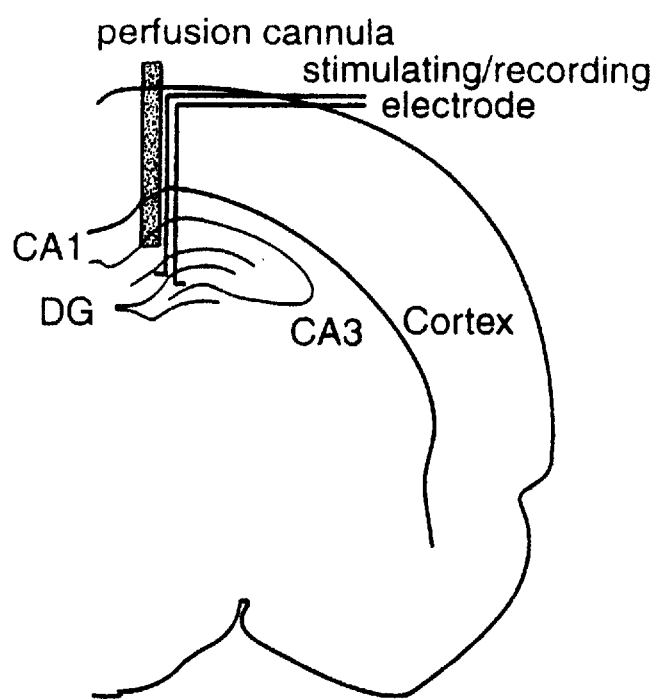
FIG. 1 is a schematic drawing of a rat model of kindling-induced epileptogenesis, showing the location of the cannula and the stimulating/recording electrode inserted into the animal in the vicinity of the dorsal hippocampus for application of electrical stimulus and administration of therapeutic material (BDNF).

Epileptic seizures induced by the application of daily electrical stimulations of the hippocampus in the brain of a rat, a phenomenon referred to as "kindling", is a validated model of epileptogenesis; Goddard et al., Experimental Neurology, Volume 25, page 295 et seq. (1969). Kindling is a non-lesionning test model for which increases in situ in the amount of both NGF and BDNF have been reported, Gall, Experimental Neurology, Volume 124, page 150 et seq. (1993). In this model, a combined electrode/cannula enables the continuous administration of a test material to the same population of neurons that are activated by the applied electrical stimulations (see FIG. 1).

A. Materials and Methods

Hippocampal kindling was carried out in male Wistar rats, each weighing about 320 to 350 grams, that were implanted with a unilateral bipolar electrode fixed on a stainless steel cannula (outer diameter 0.5 mm). Recombinant human BDNF (obtained from Amgen, Thousand Oaks, Calif.) was dissolved in a phosphate buffer solution (PBS) to a concentration of 5 micrograms per microliter (mg/ml) just prior to filling the osmotic minipumps (Alzet, model 2001 manufactured by Alza, Palo Alto, Calif.). Direct blue was added to the solution at a concentration of 0.2 mg/ml as vital staining to control the effectiveness of the perfusion. BDNF or PBS (as a control) was administered in the vicinity of the stimulating electrode at a rate of 5 mg/ml per hour for seven days, using the cannula. Kindling was performed using a standard protocol (monophasic square wave current; frequency=50 Hz, duration=2 seconds; pulse=1 millisecond), with an intensity equal to twice the threshold value (means±SEM=51.9±9.6 and 42.9±7.1 mA for controls and BDNF, respectively). See Hirsch et al., Epilepsy Research, Volume 11, page 159 et seq. (1992) for reference. The test animals were stimulated electrically in the area of the dentate gyrus and CA1 regions of the brain (see FIG. 1) once daily during the week of the perfusion, then twice daily over the next fourteen days. The behavior of the animals was scored by an observer after each electrical stimulation, and the duration of seizure afterdischarges in the hippocampus and cerebral cortex were measured. Only animals with both the correct location of the bipolar electrode in the dorsal hippocampus and staining by direct blue of cell bodies in the vicinity of the cannula tip were included in the analysis of the results.

B. Results

Figure 3A:
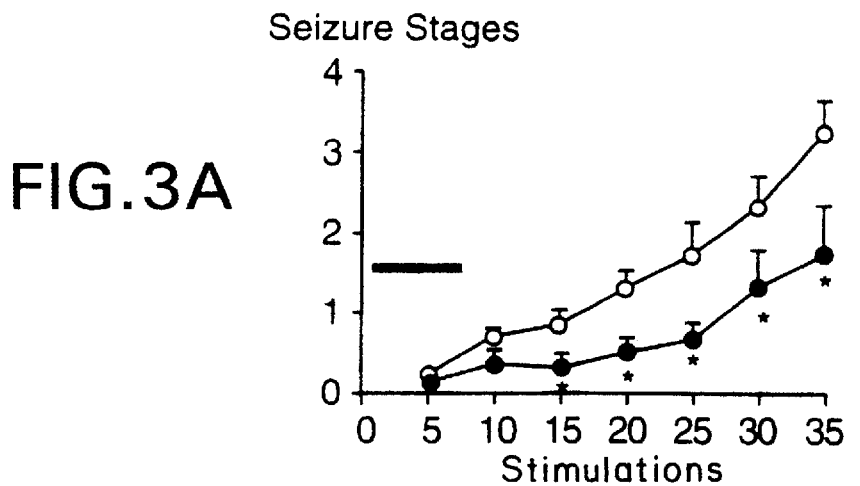
FIG. 3 depicts in graphical form the effects of a seven-day perfusion of BDNF on the development of hippocampal kindling in the same rat model. Effects on the duration of hippocampal and cortical afterdischarges are shown in panels A and B, respectively. A score based on the observation of behavioral signs (explained in the text further below) is depicted in panel C.
Figure 3B:
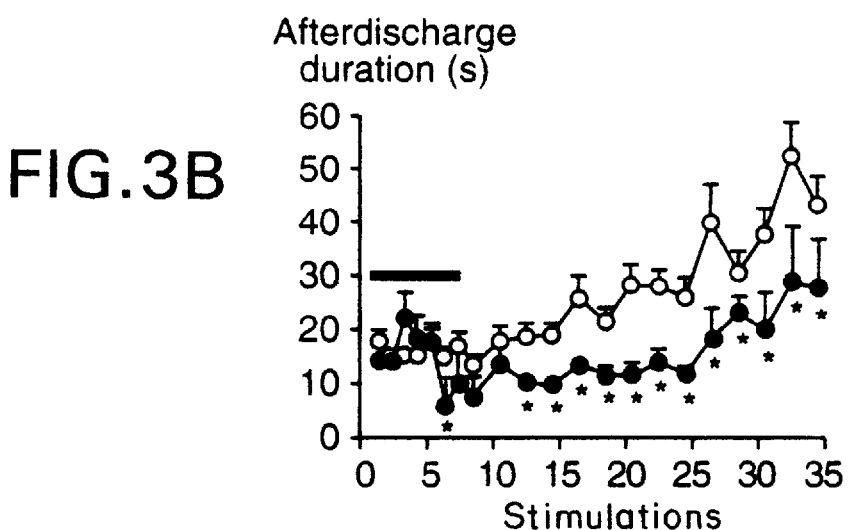
Figure 3C:
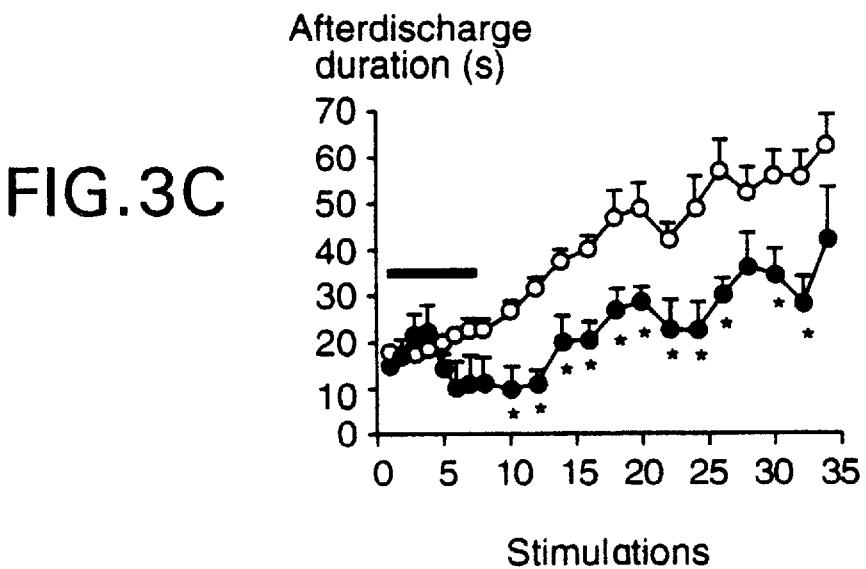

BDNF administered during the first week of electrical stimulation significantly reduced the development of seizures in the test animals, as manifested by a large reduction in the duration of hippocampal and cortical afterdischarges and the scoring of behavioral signs (see FIG. 2, panels A, B, and C). In the control group, the durations of hippocampal and cortical afterdischarges as well as seizure scoring increased progressively throughout the application of 35 electrical stimulations (FIGS. 2 and 3). By contrast, in BDNF-treated rats the durations of the hippocampal afterdischarges remained below the initial values until the 25th electrical stimulation and the duration of cortical discharges began to increase only after the 14th electrical stimulation. Moreover, BDNF-treated rats displayed a behavioral arrest without any signs of limbic seizure up until the 25th stimulation.

Daily recordings (at every sixty minutes) of both kindled and non-kindled BDNF-treated rats during the week of perfusion failed to reveal any significant modifications of the basal EEG activity as compared to a pre-perfusion reference standard. In addition, there were no signs of motor impairment or debilitation. A marked decrease in body weight (up to 30%) was observed in BDNF-treated animals during the week of perfusion as compared to the control group. However, after the perfusion period these animals gained weight progressively, although they remained under the weights of the control rats. A similar weight loss has been reported in the literature following chronic cerebral perfusions of BDNF Shen et al., Proceedings of the National Academy of Science, USA, Volume 91, page 8420 et seq. (1994). In the present study, this weight loss seemed to be due to a reduction in food intake by the animals (up to 49%). In general, BDNF-treated rats appeared to be more active, especially during the week of perfusion. This was quantified on the 5th day of perfusion by a behavioral test for general activity (open field), which revealed a significant increase in locomotion for the BDNF-treated rats as compared to the control rats (see Table 1).

TABLE 1

Behavioral Test - General Activity

| | No. of Rats Tested | Locomotion Score | Rearings Score |
| --- | --- | --- | --- |
| Control (PBS-treated) | 9 | 46.5 ± 9.7 | 18.7 ± 4.4 |
| BDNF-treated | 7 | 164.4 ± 27.1 | 28.1 ± 7.1 |

*As measured in a six minute open field test five days following commencement of perfusion. Each rat was placed in the middle of a 60-cm diameter enclosure having a floor partitioned into twelve squares of equal surface area. "Locomotion" was defined as the number of squares crossed by the rats.

Finally, a histological study of the dorsal hippocampus of BDNF-treated rats, as performed with cresyl staining, did not reveal any difference in cell body degeneration or glial cell proliferation around the tip of the cannula/electrode, in comparison to the control rats.

C. CONCLUSION

These data provide, for the first time, evidence that BDNF is involved in a long term process which tends to protect hippocampal cells against the development of epileptic seizures in the absence of any neuronal damage. These findings suggest that BDNF not only acts as a survival factor for a precise population of neurons, but it may also be involved in fine regulation of neural excitability before any neuronal damage can occur. The protective effects of exogenous BDNF against epileptogenesis described here suggests that a seizure-induced synthesis of endogenous BDNF and expression of trkB (the high affinity receptor for BDNF) within the same central nervous system neurons may reflect the self-defense process against the overexcitation of hippocampal neurons. Moreover, these results demonstrate that the application of exogenous BDNF enhances and reinforces this protective effect. Without wishing to be bound by any theory of the invention, it can be speculated that the presence of BDNF may control the expression of inhibitory neuropeptides (e.g., neuropeptide Y and somatostatin) and intracellular calcium chelators, which are themselves involved in anti-eliptogenesis. The invention is now defined with reference to the appended claims.

What is claimed is:

1. A method for treating epilepsy in a mammal, comprising administering to the mammal a therapeutically effective amount of BDNF of SEQ. ID NO: 1 sufficient to prevent, retard or ameliorate epileptic seizures in vivo.

2. The method of claim 1, in which the mammal is a human.

3. The method of claim 1, in which the BDNF is recombinant human BDNF.

4. The method of claim 3, in which the recombinant BDNF is produced in *E. coli*.

5. The method of claim 4, in which the recombinant BDNF has the amino acid sequence of SEQ ID NO:1.

6. The method of claim 1, in which BDNF is administered in the form of a pharmaceutically acceptable buffered solution.

7. The method of claim 1, in which BDNF is administered to the brain by intraparenchymal injection.

8. The method of claim 1, in which BDNF is administered to the brain by intraventricular injection.

9. A method according to claims 6 or 7, in which BDNF is administered chronically by use of an osmotic pump.

10. The method of claim 1, in which the thereutically effective amount is from about 0.02 to about 0.25 grams per kilograms of body weight per day.

* * * * *

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 120 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:1:

```
Met His Ser Asp Pro Ala Arg Arg Gly Glu Leu Ser Val Cys Asp Ser
1               5                   10                  15

Ile Ser Glu Trp Val Thr Ala Ala Asp Lys Lys Thr Ala Val Asp Met
            20                  25                  30

Ser Gly Gly Thr Val Thr Val Leu Glu Lys Val Pro Val Ser Lys Gly
        35                  40                  45

Gln Leu Lys Gln Tyr Phe Tyr Glu Thr Lys Cys Asn Pro Met Gly Tyr
    50                  55                  60

Thr Lys Glu Gly Cys Arg Gly Ile Asp Lys Arg His Trp Asn Ser Gln
65                  70                  75                  80

Cys Arg Thr Thr Gln Ser Tyr Val Arg Ala Leu Thr Met Asp Ser Lys
                85                  90                  95

Lys Arg Ile Gly Trp Arg Phe Ile Arg Ile Asp Thr Ser Cys Val Cys
            100                 105                 110

Thr Leu Thr Ile Lys Arg Gly Arg
            115                 120
```